United States Patent
Shannon et al.

(10) Patent No.: US 6,790,225 B1
(45) Date of Patent: Sep. 14, 2004

(54) STENTED, RADIALLY EXPANDABLE, TUBULAR PTFE GRAFTS

(75) Inventors: Donald T. Shannon, Mission Viejo, CA (US); Chris Kuo, Orange, CA (US); John McIntyre, Vista, CA (US); Ronald L. Clinkenbeard, Mission Viejo, CA (US); Yizi Chu, Santa Ana, CA (US); Benny Tu, Lake Forest, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/358,350

(22) Filed: Jul. 21, 1999

Related U.S. Application Data

(62) Division of application No. 08/675,644, filed on Jul. 3, 1996, now Pat. No. 5,928,279.

(51) Int. Cl.$^7$ .................................................. A61F 2/06
(52) U.S. Cl. ..................................... 623/1.13; 623/901
(58) Field of Search ............................. 623/1.13, 901, 623/909, 920, 921; 600/36; 264/127, 230, 294, 342 R

(56) References Cited

U.S. PATENT DOCUMENTS

| | | | |
|---|---|---|---|
| 4,332,035 A | 6/1982 | Mano | |
| 4,713,070 A | 12/1987 | Mano | |
| 5,098,625 A | 3/1992 | Huang | |
| 5,735,892 A | 4/1998 | Myers et al. | 623/1 |
| 5,749,880 A | * 5/1998 | Banas et al. | 606/198 |
| 5,810,870 A | 9/1998 | Myers et al. | 606/198 |
| 5,925,075 A | 7/1999 | Myers et al. | 623/1 |
| 6,042,605 A | * 3/2000 | Martin et al. | 623/1.13 |

FOREIGN PATENT DOCUMENTS

| | | |
|---|---|---|
| DE | 3918736 | * 12/1990 |
| GB | 1355373 | 5/1974 |
| GB | 1505591 | 3/1978 |
| GB | 1506432 | 5/1978 |

* cited by examiner

*Primary Examiner*—Brian E Pellegrino
(74) *Attorney, Agent, or Firm*—Rajiv Yadav

(57) ABSTRACT

Stented tubular grafts of expanded, sintered polytetrafluoroethylene (PTFE). The stented PTFE grafts of the present invention include an integrally stented embodiment, an externally stented embodiment, and an internally stented embodiment. In each embodiment, the stent may be either self-expanding or pressure-expandable. Also, in each embodiment, the stent may be coated or covered with a plastic material capable of being affixed (e.g., heat fused) to PTFE. Manufacturing methods are also disclosed by the individual components of the stented grafts are preassembled on a mandrel and are subsequently heated to facilitate attachment of the PTFE layer(s) to one another and/or to the stent. Optionally, the stented graft may be post-flexed and post-expanded following it's removal from the mandrel to ensure that the stented graft will be freely radially expandable and/or radially contractible over it's full intended range of diameters.

44 Claims, 4 Drawing Sheets

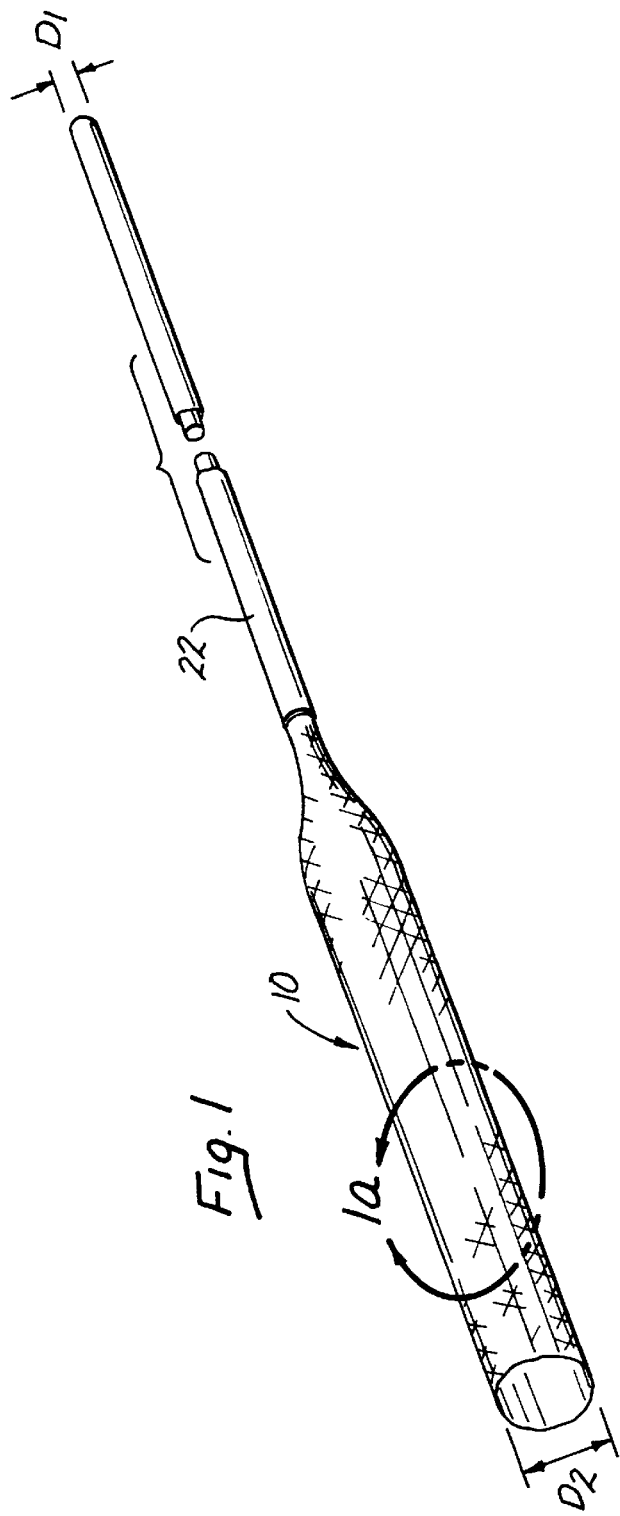
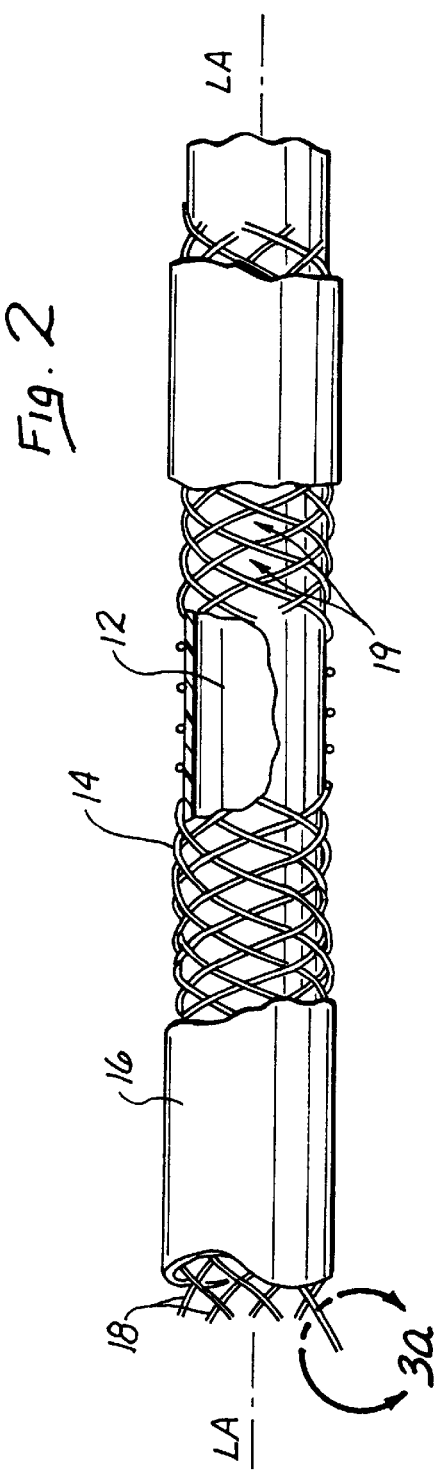

STENTED, RADIALLY EXPANDABLE, TUBULAR PTFE GRAFTS

This is a divisional application of U.S. Pat. No. 5,928,279, Ser. No. 08/675,644, filed Jul. 3, 1996.

FIELD OF THE INVENTION

The present invention pertains generally to medical devices and their methods of manufacture, and more particularly to tubular, polytetrafluoroethylene (PTFE) grafts having integral, radially expandable stents, for implantation in cavities or passageways (e.g., ducts or blood vessels) of the body.

BACKGROUND OF THE INVENTION

A. Stents

The prior art has included a number of radially expandable stents which may be initially deployed in a radially collapsed state suitable for transluminal insertion via a delivery catheter, and subsequently transitioned to a radially expanded state whereby the stent will contact and engage the surrounding wall or the anatomical duct or body cavity within which the stent has been positioned. Such stents have been used to support and maintain the patency of blood vessel lumens (e.g., as an adjuvant to balloon angioplasty) and to structurally support and/or anchor other apparatus, such as tubular endovascular grafts, at desired locations within a body cavity or passageway (e.g., to anchor a tubular endovascular graft within a blood vessel such that the graft forms an internal conduit through an aneurysm or site of traumatic injury to the blood vessel wall).

Many stents of the prior art have been formed of individual member(s) such as a wire, plastic, metal strips, or mesh which has been bent, woven, interlaced or otherwise fabricated into a generally cylindrical configuration. These stents of the prior art have generally been classified into two major categories—a) "self-expanding" stents, and b) "pressure expandable" stents.

i) Self-expanding Stents

Self-expanding stents are typically formed of spring metal, shape memory alloy, or other material which is resiliently biased toward its' fully radially expanded Configuration or otherwise capable of self-expanding to its' fully radially expanded configuration without the need for the exertion of outwardly directed radial force upon the stent by some extraneous expansion apparatus (e.g., a balloon or mechanical expander tool). These self-expanding stents may be initially radially compressed and loaded into a small diameter delivery catheter or alternatively mounted upon the outer surface of a delivery catheter equipped with some means for restraining or maintaining the stent in its' radially compressed state. Thereafter, the delivery catheter is inserted into the body and is advanced to a position where the stent is located at or near the site at which it is to be implanted. Thereafter, the stent is expelled out of (or released from) the delivery catheter and allowed to self-expand to it's full radial diameter. Such expansion of the stent causes the stent to frictionally engage the surrounding wall of the body cavity or passageway within which the stent has been positioned. The delivery catheter is then extracted, leaving the self-expanded stent at its' intended site of implantation. Some examples of self-expanding stents of the prior art include those described in U.S. Pat. No. 4,655,771 (Wallsten et al.); U.S. Pat. No. 4,954,126 (Wallsten): U.S. Pat. No. 5, 061, 275 (Wallsten et al.); U.S. Pat. No. 4,580,568 (Gianturco); U.S. Pat. No. 4,830,003 (Wolf et al.); U.S. Pat. No. 5,035,706 (Gianturco et al.) and U.S. Pat. No. 5,330,400 (Song).

ii) Pressure-Expandable Stents

The pressure-expandable stents of the prior art are typically formed of metal wire, metal strips, or other malleable or plastically deformable material, fabricated into a generally cylindrical configuration. The pressure-expandable stent is initially disposed in a collapsed configuration having a diameter which is smaller than the desired final diameter of the stent, when implanted in the blood vessel. The collapsed stent is then loaded into or mounted upon a small diameter delivery catheter. The delivery catheter is then advanced to its desired location within the vasculature, and a balloon or other stent-expansion apparatus (which may be formed integrally of or incorporated into the delivery catheter) is utilized to exert outward radial force on the stent, thereby radially expanding and plastically deforming the stent to it's intended operative diameter whereby the stent frictionally engages the surrounding blood vessel wall. The material of the stent undergoes plastic deformation during the pressure-expansion process. Such plastic deformation of the stent material causes the stent to remain in its radially expanded operative configuration. The balloon or other expansion apparatus is then deflated/collapsed and is withdrawn from the body separately from, or as part of, the delivery catheter, leaving the pressure-expanded stent at it's intended site of implantation.

Some examples of pressure-expandable stents of the prior art include those described in U.S. Pat. No. 5,135,536 (Hillstead); U.S. Pat. No. 5,161,547 (Tower); U.S. Pat. No. 5,292,331 (Boneau); U.S. Pat. No. 5,304,200 (Spaulding) and U.S. Pat. No. 4,733,665 (Palmaz).

B. PTFE Vascular Grafts

Fluoropolymers, such as polytetrafluoroethylene, have been heretofore used for the manufacture of various types of prosthetic vascular grafts. These vascular grafts are typically of tubular configuration so as to be useable to replace an excised segment of blood vessel.

The tubular PTFE vascular grafts of the prior art have traditionally been implanted, by open surgical techniques, whereby a diseased or damaged segment of blood vessel is surgically excised and removed, and the tubular bioprosthetic graft is then anastomosed into the host blood vessel as a replacement for the previously removed segment thereof. Alternatively, such tubular prosthetic vascular grafts have also been used as bypass grafts wherein opposite ends of the graft are sutured to a host blood vessel so as to form a bypass conduit around a diseased, injured or occluded segment of the host vessel.

In general, many tubular prosthetic vascular grafts of the prior art have been formed of extruded, porous PTFE tubes. In some of the tubular grafts of the prior art a PTFE tape is wrapped about and laminated to the outer surface of a tubular base graft to provide reinforcement and additional burst strength. Also, some of the prior tubular prosthetic vascular grafts have included external support member(s), such as a PTFE beading, bonded or laminated to the outer surface of the tubular graft to prevent the graft from becoming compressed or kinked during implantation. These externally supported tubular vascular grafts have proven to be particularly useful for replacing segments of blood vessel which pass through, or over, joints or other regions of the body which undergo frequent articulation or movement.

One commercially available, externally-supported, tubular vascular graft is formed of a PTFE tube having a PTFE filament helically wrapped around, and bonded to, the outer surface of the PTFE tube. (IMPRA Flex™ Graft, IMPRA, Inc., Tempe, Ariz.)

One other commercially available, externally-supported, tubular vascular graft comprises a regular walled, PTFE tube which has PTFE reinforcement tape helically wrapped around, and bonded to, the outer surface of the PTFE tube and individual rings of Fluorinated Ethylene Propylene (FEP) rings disposed around, and bonded to, the outer surface of the reinforcement tape. (FEP ringed ePTFE vascular graft, W. L. Gore & Associates, Inc., Flagstaff, Ariz.)

C. Stented Grafts

The prior art has also included a number of "stented grafts". These stented grafts typically comprise a self-expanding or pressure-expandable stent which is affixed to or formed within a pliable tubular graft. Because of their radial compressibility/expandability, these stented grafts are particularly useable in applications wherein it is desired to insert the graft into an anatomical passageway (e.g., blood vessel) while the graft is in a radially compact state, and to subsequently expand and anchor the graft to the surrounding wall of the anatomical passageway.

More recently, methods have been developed for introducing and implanting tubular prosthetic vascular grafts within the lumen of a blood vessel, by percutaneous or minimal incision means. Such endovascular implantation initially involves translumenal delivery of the graft, in a compacted state, by way of a catheter or other translumenally advancable delivery apparatus. Thereafter, the graft is radially expanded and anchored to the surrounding blood vessel wall, thereby holding the graft at its intended site of implantation within the host blood vessel. An affixation apparatus such as a stent, is typically utilized to anchor at least the opposite ends of the tubular graft to the surrounding blood vessel wall. One particular application for endovascular grafts of this type is in the treatment of vascular aneurysms without requiring open surgical access and resection of the aneurysmic blood vessel. Also, such stented grafts may also be useable to treat occlusive vascular disease—especially in cases where the stented graft is constructed in such a manner that the tubular graft material forms a complete barrier between the stent and the blood which is flowing through the blood vessel. In this manner the tubular graft material may serve as a smooth, biologically compatible, inner "covering" for the stent, thereby preventing a) turbulent blood-flow as the blood flows over the wire members or other structural material of which the stent is formed, b) immunologic reaction to the metal or other material of which the stent is formed, and c) a barrier to separate a diseased or damaged segment of blood vessel from the blood-flow passing therethrough. Such prevention of turbulent blood-flow and/or immunologic reaction to the stent material is believed to be desirable as both of these phenomena are believed to be associated with thrombus formation and/or restenosis of the blood vessel.

Other uses for stented grafts may include restoring patency to, or re-canalizing, other anatomical passageways such as ducts of the biliary tract, digestive tract and/or genito-urinary tract.

Many of the stented grafts known in the prior art have utilized woven or knitted material, such as polyester fiber, as the graft material.

There exists a need for the development of a radially expandable, stented graft formed of a continuous, tubular ePTFE tube because the inherent properties of PTFE may offer various clinical advantages over the woven polyester and other graft materials which have been previously used in stented grafts of the prior art.

SUMMARY OF THE INVENTION

The present invention is directed to stented, tubular, PTFE grafts and their methods of manufacture. In general, the present invention may exist in any of three (3) separate embodiments, depending upon whether the stent component of the graft is formed integrally (i.e., within) the tubular PTFE graft, externally (i.e., on the outer surface of) the tubular PTFE graft, or internally (i.e., on the inner lumenal surface) of the PTFE tubular graft. Each of these three separate embodiments of the invention may be self expanding (i.e., incorporating a self-expanding stent) or pressure-expandable (i.e., incorporating a pressure-expandable stent).

In accordance with a first embodiment of the invention, there is provided an integrally stented PTFE graft which comprises a tubular PTFE base graft preferably of a density less than 1.6 g/cc, a radially expandable stent surrounding the outer surface of the tubular base graft, and an outer PTFE layer having a density of less than 1.6 g/cc. The tubular outer layer is fused to the tubular base graft through lateral openings or perforations formed in the stent. A polymer coating, such as a PTFE coating, may be disposed on the stent to further facilitate fusing or boding of the stent to the base tube and/or outer tubular layer.

In accordance with a second embodiment of the invention, there is provided an externally stented, tubular PTFE graft which comprises a radially compressible/expandable stent having a ePTFE tube of less than 1.6 g/cc density coaxially disposed within the stent, with the outer surface of the tubular ePTFE graft being fused or attached to the stent. A polymer coating, such as PTFE or any other plastic which may be fused or adhered to PTFE, may be applied to or formed on the stent to facilitate the desired fusion or attachment of the tube graft to the stent, and/or to improve the biocompatibility of the stent.

In accordance with a third embodiment of the invention, there is provided an internally stented, tubular PTFE graft comprising a tubular outer layer formed of ePTFE having a density of less than 1.6 g/cc, and a radially expandable stent. The stent is coaxially disposed within the lumen of the tubular outer layer, and fused or attached thereto. The stent may be covered with a polymer coating, such as PTFE or other biocompatable plastic capable of adhering or fusing to PTFE, to facilitate the desired fusion or attachment of the stent to the outer tubular layer, and/or to improve the biocompatability of the stent. Additionally or alternatively, PTFE particles may be disposed between the tubular outer layer and the tubular base graft to facilitate adhering or fusing of these two layers to one another, and/or to the stent. Such PTFE particles may be disposed between the inner base graft and outer tubular layer by applying or depositing PTFE liquid dispersion therebetween, or by depositing dry PTFE resin powder therebetween.

Any of above-summarized three (3) separate embodiments of the invention may be manufactured by a method which comprises the steps of: a) initially positioning a generally cylindrical stent of either the self-expanding or pressure-expandable variety in contacting coaxial relation with the tubular ePTFE base graft and/or the tubular ePTFE outer layer, upon a cylindrical mandrel or other suitable support surface, and b) subsequently fusing the fuse (i.e., heating to a lamination temperature) assembled components (i.e., the stent in combination with the inner base graft and/or outer tubular layer) of the stented graft into a unitary stented graft structure. In integrally stented embodiments where both the tubular ePTFE base graft and the tubular ePTFE outer layer are present, such heating will. additionally cause the tubular outer layer to fuse to the inner tubular base graft, through lateral openings or perforations which exist in the stent. The stent may be surface treated, abraded, or coated with a plastic capable of adhering or fusing to ePTFE to facilitate attachment of the stent to the adjacent outer layer and/or inner base graft upon subsequent heating, application of solvent or other suitable adhesion promoting technique. In instances where a plastic coating is formed on the stent, such coating may be in the nature of a tube or film which is applied to the stent prior to assembly and mounting of the stented graft components on the mandrel or other support surface. Also, in embodiments where both the outer tubular layer and tubular base graft are used, aqueous PTFE dispersion, powdered PTFE resin or other flowable plastic material, may be deposited between the outer tubular layer and inner tubular base graft at the time of assembly (prior to heating) to further facilitate fusion of the outer tubular layer and/or inner tubular base graft to the stent and/or to one another.

By the above-described materials and methods of construction, the stented PTFE grafts of the present invention are capable of radially expanding and contracting without excessive puckering, wrinkling or invagination of the PTFE graft material. Furthermore, in embodiments wherein the stent is constructed of individual members which move or reposition relative to one another during respective expansion and contraction of the stented graft, the manufacturing methods and materials of the present invention render the PTFE sufficiently strong and sufficiently firmly laminated or fused so as to permit such relative movement of the individual members of the stent without tearing or rupturing of the tubular PTFE graft.

Further objects and advantages of the invention will become apparent to those skilled in the art upon reading and understanding the following detailed description and the accompanying drawings.

BRIEF DESCRIPTION OF THE DRAWINGS

FIG. 1 is a perspective view of an integrally stented PTFE tubular graft of the present invention, wherein a portion of the graft has been inserted into a tubular catheter.

FIG. 2 is an enlarged, cut-away, elevational view of a preferred, integrally stented, tubular PTFE graft of the present invention.

FIG. 3b is an enlarged cross-sectional view through line 3b–3d of FIG. 3a.

DETAILED DESCRIPTION OF THE PREFERRED EMBODIMENTS

Figure 1A:
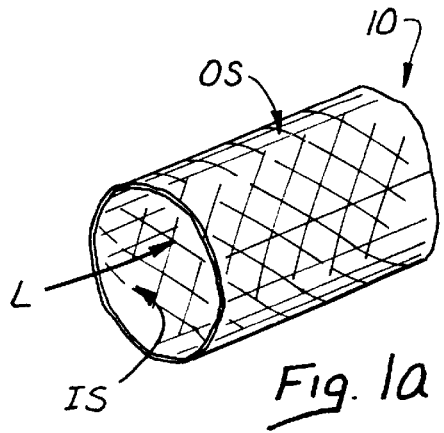
FIG. 1a is an enlarged perspective view of a segment of FIG. 1.
Figure 3A:
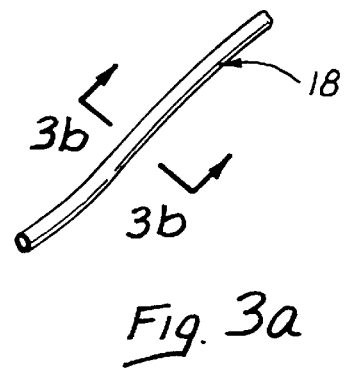
FIG. 3a is an enlarged perspective view of a portion of the stent incorporated in the graft of FIG. 2.
Figure 3B:
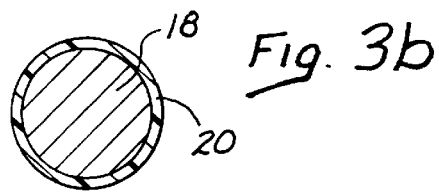

The following detailed description is provided for the purpose of describing and illustrating presently preferred embodiments of the invention only, and is not intended to exhaustively describe all possible embodiments in which the invention may be practiced.

A. The Structure of an Integrally Stented PTFE Graft

With reference to FIGS. 1–3b, there is shown an integrally stented tubular PTFE graft 10 of the present invention. The preferred integrally stented graft 10 comprises a tubular PTFE base graft 12, a PTFE-coated stent 14 and an outer layer of PTFE 16.

One of the many types of stents which may be used to form the stent 14 component of a stented graft 10 of the present invention, is shown in the drawings. This particular stent 14 is formed of individual elements or wires 18 which have been coated with a PTFE coating 20. Gaps or lateral openings 19 exist between adjacent ones or bundles of the wires 18. The configuration, construction, and function of this stent 14 is described in detail in U.S. Pat. No. 4,655,771 Wallsten); U.S. Pat. No. 4,954,126 (Wallsten); and U.S. Pat. No. 5,061,275 (Wallsten et al.), the entireties of which are hereby expressly incorporated herein by reference. As shown in the figures of this patent application, this particular stent 14 is composed of rigid but resiliently flexible thread elements or wires 18. These thread elements or wires 18 are formed of metal, such as an alloy of cobalt, chromium, nickel or molybdenum, wherein the alloying residue is iron. One specific example of a commercially available alloy which may is usable to form the wires 18 of the stent 14 is Elgiloy (The Elgiloy Company, 1565 Fleetwood Drive, Elgin, Ill. 60120). The wires 18 of this stent 14 are arranged in helical configuration about a common longitudinal axis LA. A number of the wires 18 are positioned in substantially parallel relation to one another, but are axially displaced relative to each other. By such arrangement, some of the wires 18 are wound in a first helical direction, while others are wound in a second or opposite helical direction such that they cross on opposite sides of adjacent ones of the wires wound in the first helical direction so as to form a helically braided wire stent as shown in the Figures. This results in the formation of a braided wire stent 14 of generally tubular configuration which is self-expanding and biased to it's radially expanded diameter $D_2$. However, this stent 14 may be radially compressed to a smaller diameter $D_1$ and radial constraint, as may be applied by the surrounding wall of the tubular delivery catheter 22 shown in FIG. 1, may be applied to hold the stent 14 in such radially compressed state (diameter $D_1$). Thereafter, when the radial constraint is removed from the stent 14, the stent 14 will resiliently spring back to its radially expanded diameter $D_2$. The individual, helically wound wires 18 of this particular braided stent 14 move and articulate such that the angular dispositions of the wires 18, relative to one another, will change radial expansion and compression of the stent 14. Also, the longitudinal length of the stent 14 will increase as the stent 14 is radially compressed toward its radially compact configuration $D_1$, and such length will shorten as the stent 14 expands toward its radially expanded configuration $D_2$. Thus, is the optional PTFE coating 20 is applied to the wires 18 of the stent 14, such coating (described in detail herebelow) is preferably flexible enough to withstand the flexing and movement of the individual wires 18 without cracking or degrading.

The tubular base graft 12 is initially coaxially positioned within the hollow inner bore of the tubular stent 14 while the stent 14 is in it's radially expanded configuration, after the stent 14 has been coated with the PTFE coating 20, if desired. Thereafter, the outer PTFE layer 16 is formed by any suitable means, such as by wrapping PTFE tape 17 upon the outer surface of the PTFE coated stent 14 to form the generally tubular outer PTFE layer 16. Thereafter, heat or other means are utilized to fuse the outer PTFE layer 16 to the inner base graft 12, through the gaps or openings 19 which exist in the stent 14. In embodiments wherein the optional PTFE coating 20 has been applied to the stent 14, such heating will also facilitate bonding of the PTFE coating 20 of the stent 14 to the adjacent base graft 12 and outer PTFE layer 16. In this manner, there is formed a self-expanding, tubular, integrally stented, PTFE graft 10 of substantially unitary construction. The stent 14 forms an integral structural framework within the tubular graft 10, and the fused PTFE body of the graft is low enough in density and sufficiently pliable to allow the stent 14 incorporated into the graft 10 to continue to undergo substantially the same range of radial expansion and contraction that such stent 14 was capable of before disposition, of the PTFE graft thereon. In this regard, the internally stented graft 10 is radially compressible to the stent's first diameter $D_1$ and may be may be inserted into the lumen of a small diameter tubular catheter 22. The external constraint provided by the wall of the catheter 22 will maintain the stented graft 10 in it's radially compressed configuration of diameter $D_1$ until such time as the graft 10 is expelled or ejected out of the catheter 22. After the graft 10 has been expelled or ejected out of the catheter 22, the graft will self-expand to a diameter which is substantially equal to the original expanded diameter $D_2$ of the stent 14.

B. Preparation of the Tubular Base Graft i.) Preparation of Paste

The manufacture of the tubular base graft begins with the step of preparing a PTFE paste dispersion for subsequent extrusion. This PTFE paste dispersion may be prepared by known methodology whereby a fine, virgin PTFE powder (e.g., F-104 or F-103 Virgin PTFE Fine Powder, Dakin America, 20 Olympic Drive, Orangebury, N.Y. 10962) is blended with a liquid lubricant, such as odorless mineral spirits (e.g., Isopar®, Exxon Chemical Company, Houston, Tex. 77253-3272), to form a PTFE paste of the desired consistency.

ii.) Extrusion of Tube

The PTFE-lubricant blend dispersion is subsequently passed through a tubular extrusion dye to form a tubular extrudate.

iii.) Drying

The wet tubular extrudate is then subjected to a drying step whereby the liquid lubricant is removed. This drying step may be accomplished at room temperature or by placing the wet tubular extrudate in an oven maintained at an elevated temperature at or near the lubricant's dry point for a sufficient period of time to result in evaporation of substantially all of the liquid lubricant.

iv.) Expansion

Thereafter, the dried tubular extrudate is longitudinally expanded or longitudinally drawn at a temperature less than 327° C. and typically in the range of 250–326° C. This longitudinal expansion of the extrudate may be accomplished through the use of known methodology, and may be implemented by the use of a device known as a batch expander. Typically, the tubular extrudate is longitudinally expanded by an expansion ratio of more than two to one (2:1) (i.e., at least two (2) times its original length).

Preferably, the base graft 12 is formed of expanded, sintered PTFE having a density of less than 1.6 grams per cubic centimeter.

v.) Sintering

After the longitudinal expansion step has been completed, the expanded PTFE tube is subjected to a sintering step whereby it is heated to a temperature above the sintering temperature of PTFE (i.e., 350–370° C.) to effect amorphous-locking of the PTFE polymer. The methodology used to effect the sintering step, and the devices used to implement such methodology, are known in the art.

Completion of the sintering step marks the completion of the preparation of the expanded, sintered PTFE base graft 12.

The PTFE tape 16 may be manufactured by any suitable method, including the general method for manufacturing expanded PTFE tape, as follows:

C. Preparation of PTFE Tape i.) Preparation of Paste Dispersion

The usual manufacture of an expanded, sintered PTFE tape 17 useable to form the outer PTFE layer 16 of the stented graft 10 begins with the preparation of a PTFE paste dispersion. This PTFE paste dispersion may be prepared in the same manner as described hereabove for preparation of the PTFE paste dispersion used to form the tubular base graft.

ii.) Extrusion of Film

The PTFE paste dispersion is subsequently passed through the film extrusion dye to form a wet film extrudate. The wet film extrudate is taken up or wound upon a rotating core so as to form a roll of the wet film extrudate.

iii.) Calendaring

The wet film extrudate is subsequently unrolled and subjected to an initial cold (i.e., <100° C.) calendaring step by passing the film through at least one set of opposing stainless steel calendaring rollers having an adjustable gap thickness therebetween. The calendaring rollers are preferably maintained at a temperature between room temperature and 60° C. The width of the wet extrudate is held constant as it passes through these calendaring rollers. The thickness of the wet film extrudate is reduced to its desired final thickness (e.g., 0.004–0.005 inches) while the width of the film is maintained constant. It will be appreciated that, since the width of the film is maintained constant, the passage of the film through the calendaring machine will result in a longitudinal lengthening of the film. The amount of longitudinal lengthening will be a function of the decrease in film thickness which occurs as the film passes between the calendaring rollers.

One example of a commercially available calendaring machine useable for this purpose is the small Killion 2 Roll Stack, (Killion Extruders, Inc., Cedar Grove, N.J. 07009.)

iv) Drying

Thereafter, the wet film is subjected to a drying step. This drying step may be accomplished by permitting or causing the liquid lubricant to evaporate from the matrix of the film. Such evaporation of the liquid lubricant may be facilitated by passing the film over a drum or roller which is maintained in an elevated temperature sufficient to cause the liquid lubricant to fully evaporate from the film matrix.

v) Expansion

Separately, or concurrently with the drying step the film is subjected to an expansion step. Such expansion step comprises expanding the PTFE film in at least one direction (e.g., longitudinally). Such expansion of the film serves to a) increase the porosity of the film, b) increase the strength of the film, and c) orient the PTFE fibrils in the direction of the axis of expansion.

This expansion step is typically carried out with some heating of the film during such expansion, but such heating does not exceed the crystalline melting point of the PTFE polymer.

vi) Sintering of the Film

After the drying step and expansion step have been completed, the film is subjected to a sintering step wherein the film is heated to a temperature above the melting point of PTFE to accomplish sintering or amorphous locking of the PTFE polymer. This sintering step may be carried out by passing the film over a drum or roller which is maintained at a high surface temperature (e.g., 350—420° C.) to cause the desired heating of the PTFE film above the melting point of the PTFE polymer for a sufficient period of time to effect the desired sintering of the film.

vii) Cutting the Film Into Strips

After the film has been dried, the film is cut into strips, each strip typically having a width of 0.25–0.50 inches, thereby creating strips of expanded, sintered PTFE tape 14.

D. Coating of the Stent and/or Deposition of PTFE Between Layers to Enhance Bonding Prior to assembly of the components of the integrally stented graft 10, the stent 14 may be coated with a polymer coating 20.

The polymer coating formed on the stent 14 may be any suitable type of polymer which will adhere to PTFE. Examples of polymers which may be used for such polymer coating or covering include polytetrafluoroethylene (PTFE), fluorinated ethylene propylene (FEP), polytetrafluoroethylene-perfluoroalkyl vinyl ether copolymer (PFA), polyvinyl chloride (PVC), polypropylene (PP), polyethylene terephthalate (PET) polyvinylidene fluoride (PVDF) and other biocompatable plastics.

Figure 4A:
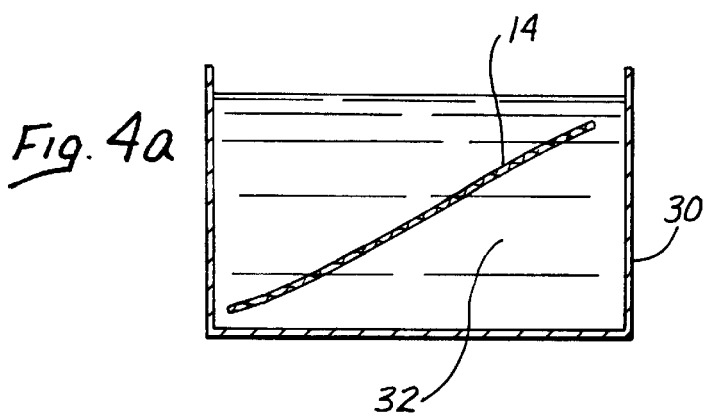
FIGS. 4a–4f are a step-by-step illustration of a preferred method for manufacturing an integrally stented PTFE graft of the present invention.

One manner in which such coating of the stent 14 may be carried out is illustrated in FIG. 4a. As shown in FIG. 4a, the stent 14 may be immersed in a vessel 30 containing an aqueous dispersion of PTFE 32. One aqueous PTFE dispersion which may be useable for coating of the stent 14 is Dupont T-30 Aqueous PTFE dispersion, available commercially from the E.I. DuPont de Nemours Co., (Wilmington, Delaware). Another commercially available PTFE dispersion 32 which may be utilized for coating of the stent is Daikin-Polyflon TFE Dispersion, available PTFE dispersion 32 which may be utilized for coating of the stent is Dakin-polyflon TFE Dispersion, available from Daikin Industries, Ltd., Chemical Division (Umeda Center Bldg., 4–12 chome, Nakazaki-nishi, Kita-ku, Osaka, Japan).

The time in which the stent 14 must remain immersed in the liquid PTFE dispersion 32 may vary, depending on the construction of the stent 14 and the chemical composition of the PTFE dispersion 32. However, in most cases, an immersion time of 10–15 seconds will be sufficient to obtain uniform deposition of the PTFE coating 20 on the wire members 18 of the stent 14.

After the stent 14 has been removed from the liquid PTFE dispersion 32, it will be permitted to air dry such that a dry PTFE coating 20 remains deposited upon the outer surface of each wire 18 of the stent 14.

Figure 5:
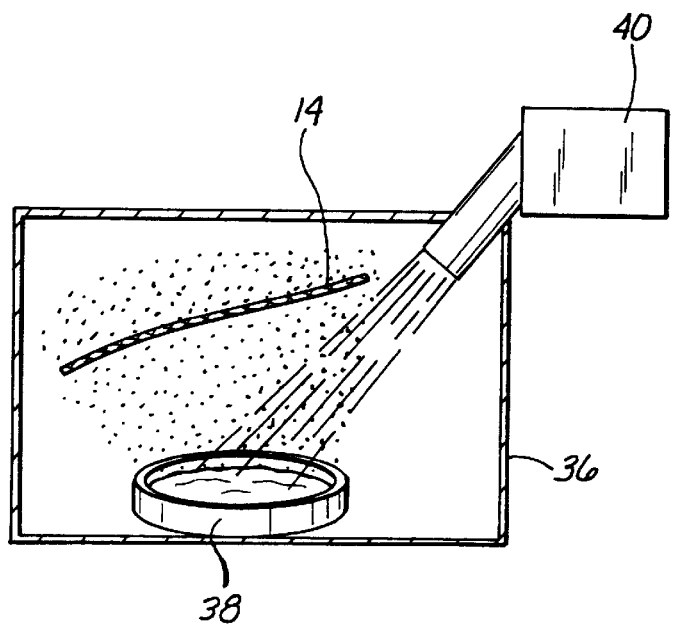
FIG. 5 is a schematic illustration of an alternative electron beam deposition method which is usable for depositing PTFE coating on the stent portion of the integrally stented PTFE grafts of the present invention.

Optionally, after the air drying has been completed, the PTFE coated stent 14 may be placed in an oven at 350° C. for approximately 10 minutes to sinter the PTFE coating and/or to enhance the bonding of the PTFE coating 20 to wire members 18 of the stent 14. Sintering of the PTFE coating renders the coating more resistant to abrasion or peeling during the subsequent handing of the stent and/or the ensuing manufacture and use of the stented graft 10. It will be appreciated that various alternative methods, other than immersion, may be used for depositing the PTFE coating 20 on the stent 14. One alternative method is electron beam deposition, as illustrated in FIG. 5. In accordance with this alternative PTFE deposition method, the stent 14 is positioned within a closed vacuum chamber 36 wherein a mass of PTFE 38 is located. An electron beam apparatus 40 is then utilized to project electron beam radiation onto the PTFE 38 within the chamber 36 so as to cause sublimation of the PTFE and resultant deposition of the layer 20 of PTFE on the outer surface of the stent 14. The apparatus and specific methodology useable to perform this electron beam deposition of the PTFE coating 20 are well known to those of skill in the relevant art.

As with the above-described immersion process (FIG. 4a), the stent 14 whereupon the PTFE coating 20 has been deposited may be subjected to optional heating at 350° C. for a period of approximately ten minutes in order to sinter the PTFE coating and/or to enhance the bonding of the PTFE coating 20 to the wire members 18 of the stent 14.

As an alternative to coating of the stent, or in addition thereto, such PTFE aqueous dispersion may be painted onto the outer surface of the base graft 12, or the inner surface of the outer tubular layer 16, or may be otherwise disposed between the base graft 12 and outer tubular layer 16 to facilitate fusion or bonding of the inner base graft 12 to the outer tubular layer 16. Or, such PTFE aqueous dispersion may be sprayed or otherwise applied to the outer surface of the outer tubular layer 16 provided that the PTFE present in the dispersion are small enough to migrate inwardly through pores in the outer tubular layer 16, thereby becoming deposited between the outer tubular layer 16 and the inner base graft 12.

Another alternative or additional means by which adherence or fusion of the base graft 12, outer tubular layer 16 and/or stent 14 may be facilitated or enhanced includes the deposition of raw PTFE resin powder between the outer tubular layer 16 and inner base graft 12, and/or upon the stent 14.

It will be appreciated that in many cases, it will be desirable to apply the polymer coating 20 to the stent 14 while the stent 14 is in it's fully radially expanded configuration of diameter $D_2$. In this manner, after the coating 20 has been applied and formed on the fully radially expanded stent 14, the stent 14 may subsequently be contracted to it's radially compact configuration of diameter $D_1$ without tearing or disrupting of the previously-applied coating 20. In embodiments which utilize a pressure-expandable stent 14, it may thus be necessary to volitionally or purposely expand the stent 14 to it's fully radially expanded diameter $D_2$ prior to application of the coating 20. Alternatively, when the stent 14 is of the self-expanding variety it will, in most cases, automatically assume it's fully radially expanded configuration of diameter $D_2$ and no such volitional or purposeful pre-expansion of the stent 14 will be required.

The preferred means by which liquid PTFE dispersion and/or solid PTFE powder may be deposited between the outer tubular layer 16, and inner base graft 12 will be discussed in more detail herebelow with reference to the manufacturing methodology.

E. Assembly and Construction of the Integrally Stented PTFE Graft

FIGS. 4b–4f show, in step-wise fashion, the preferred method for assembling and constructing the integrally stented PTFE graft 10.

Figure 4B:
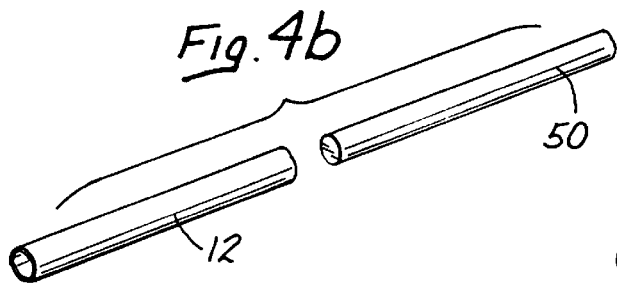

As shown in FIG. 4b, the tubular base graft 12 is initially disposed on a rod or mandrel 50. Such rod or mandrel 50 may comprise a stainless steel rod having an outer diameter which is only slightly smaller than the inner diameter of the tubular base graft 12. In this manner, the tubular base graft 12 may be slidably advanced onto the outer surface of the mandrel 50 without undue effort or damage to the base graft 12.

Figure 4C:
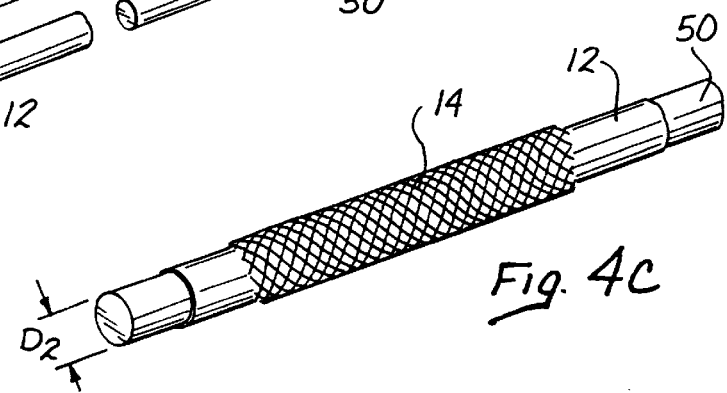

Thereafter, the PTFE-coated stent 14 is axially advanced onto the outer surface of the tubular base graft 12, as shown in FIG. 4c.

At this point in the process, PTFE liquid dispersion or powdered PTFE resin may be additionally (optionally)

applied to the stent 14 and/or outer surface of the base graft 12 to promote further bonding and fusion of the base graft 12 to the stent 14 and/or subsequently applied outer layer 16. In this regard, the mandrel-borne tubular base graft 12 and stent 14 may be rolled in powdered PTFE resin to accomplish the desired deposition of PTFE powder thereon. Alternatively, the above-described PTFE liquid dispersion may be painted sprayed or otherwise applied to the surface of the stent 14 and/or outer surface of the tubular base graft 12 prior to subsequent application of the outer tubular layer 16.

Figure 4D:
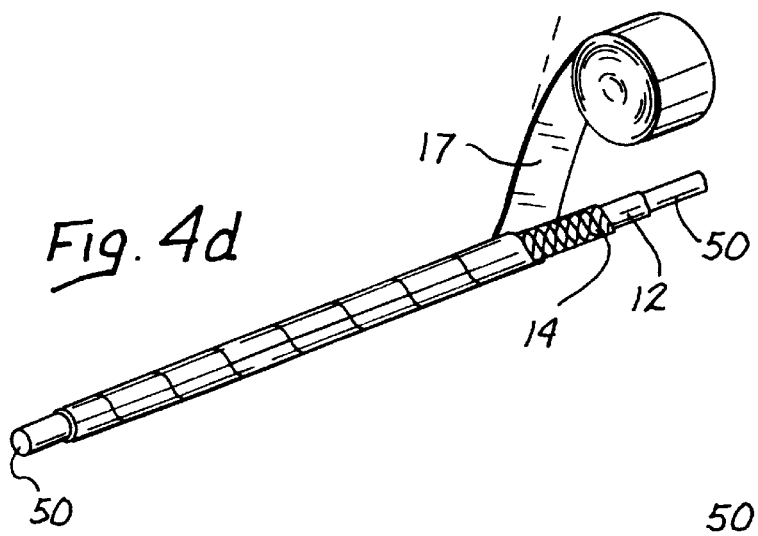

Thereafter, as shown in FIG. 4d, the tape 17 is initially helically wrapped in overlapping fashion, on the outer surface of the stent 14, in a first direction. In the preferred embodiment, tape of ½ inch width is used. The tape is helically wrapped about the stent at a pitch angle whereby 6 to 8 revolutions of the tape are applied per linear inch of the stent 14.

Figure 4E:
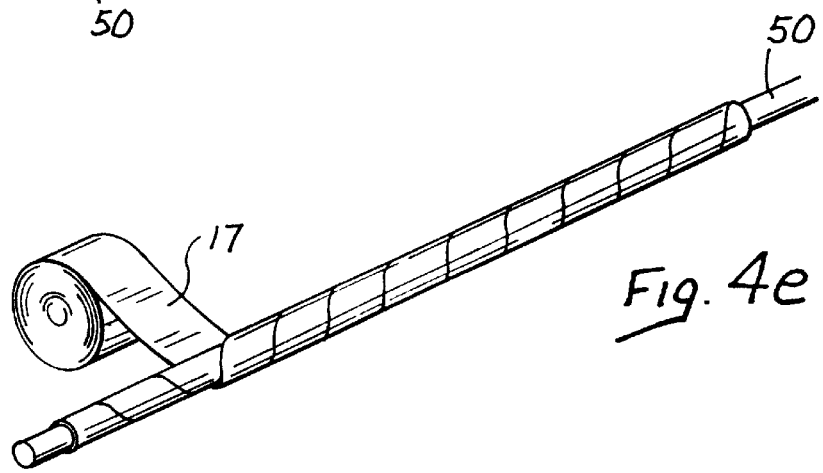

Thereafter, as shown in FIG. 4e, a second tape wrap in the opposite direction is accomplished, preferably using the same width of tape at the same pitch angle, thereby applying another 6–8 revolutions of tape 17 per linear inch of stent 14. In this manner, both wrappings of the tape 17 (FIGS. 4d and 4e) combine to form a tubular, outer PTFE layer 16 which preferably has a thickness of less than 0.1 inches, and which may be formed of 1 to 10 consecutive (e.g., laminated) layers of the tape 17. for example, when using ePTFE tape of less than 1.6 g/cc density and ½ inch width, the first helical wrap (FIG. 4d) may deposit four consecutive layers of tape 17 and the second helical wrap (FIG. 4e) may deposit an additional 4 layers of tape 17, thereby resulting in an outer tubular layer 16 which is made up of a total of 8 layers of such tape 17.

Optionally, to further promote bonding of the outer tubular layer 16 to the stent 14 and/or inner base graft 12, liquid PTFE dispersion may be sprayed, painted or otherwise applied to and dried upon the tape 17 prior to wrapping, or such liquid PTFE dispersion may be deposited by any suitable means (spraying, painting, etc.) between the outer tubular layer 16 formed by the helically wrapped tape 17 and the inner base graft 12. Or such liquid PTFE dispersion may be sprayed onto or otherwise applied to the outer surface of the helically wrapped tape 17 such the small particles of PTFE contained within the liquid dispersion will migrate inwardly through pores in the layers of tape 17, and will thereby become deposited between the outer tubular layer 16 and the inner base graft 12 prior to subsequent heating of the assembly, as described herebelow. Another alternative (and optional) method for depositing polymer (e.g., PTFE) particles between the base graft 12 and outer tubular layer 16 is by rolling the mandrel 50, having the base graft 12 and stent 14 disposed thereon, in dry, powdered polymer resin (e.g., the above-described PTFE resin) to cause such dry polymer resin to become deposited on the outer surface of the base graft 12 and/or stent 14 prior to application of the tape 17 as shown in FIGS. 4d and 4e.

Figure 4F:
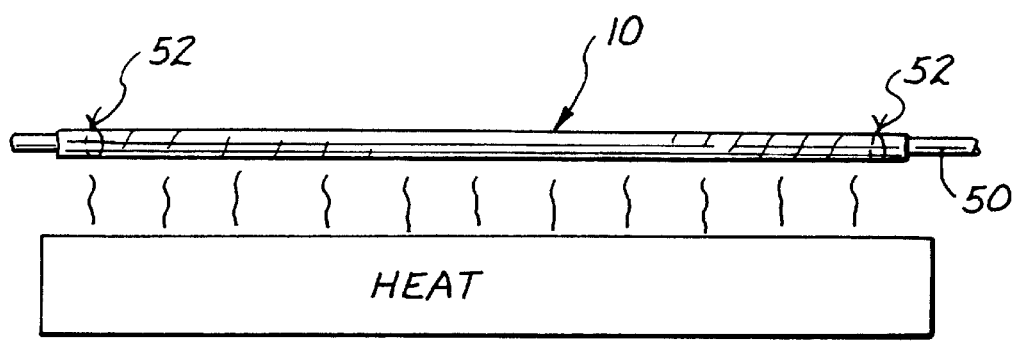

Thereafter, as shown in FIG. 4f, ligatures 52 of stainless steel wire are tied about the opposite ends of the graft 10 so as to securely hold the base graft 12, PTFE-coated stent 14 and outer layer 16 on the mandrel 50. The mandrel, having the graft 10 disposed thereon is then heated to a temperature of 363°±2° C. for thirty minutes. Such heating will cause the outer PTFE layer 16 to heat fuse to the inner base graft 12 through the openings 19 which exist in the stent 14, and will further facilitate bonding or fusing of the PTFE coating 20 of the stent 14 to the adjacent base graft 12 and outer tape layer 16. In this manner, the desired integrally-stented PTFE tubular graft 10 is formed.

The heating step illustrated schematically in FIG. 4f may be carried out by any suitable means. For example, the mandrel 50 having the graft 10 and ligatures 52 disposed thereon may be placed in an oven preheated to the desired temperature, for the desired period of time. Alternatively, the mandrel, having the graft 10 and ligatures 52 disposed thereon may be rolled on a hot plate or heated surface to accomplish the desired heat fusing or bonding of the outer layer 16, base graft 12 and PTFE coating 20 of the stent 14.

Figure 6:
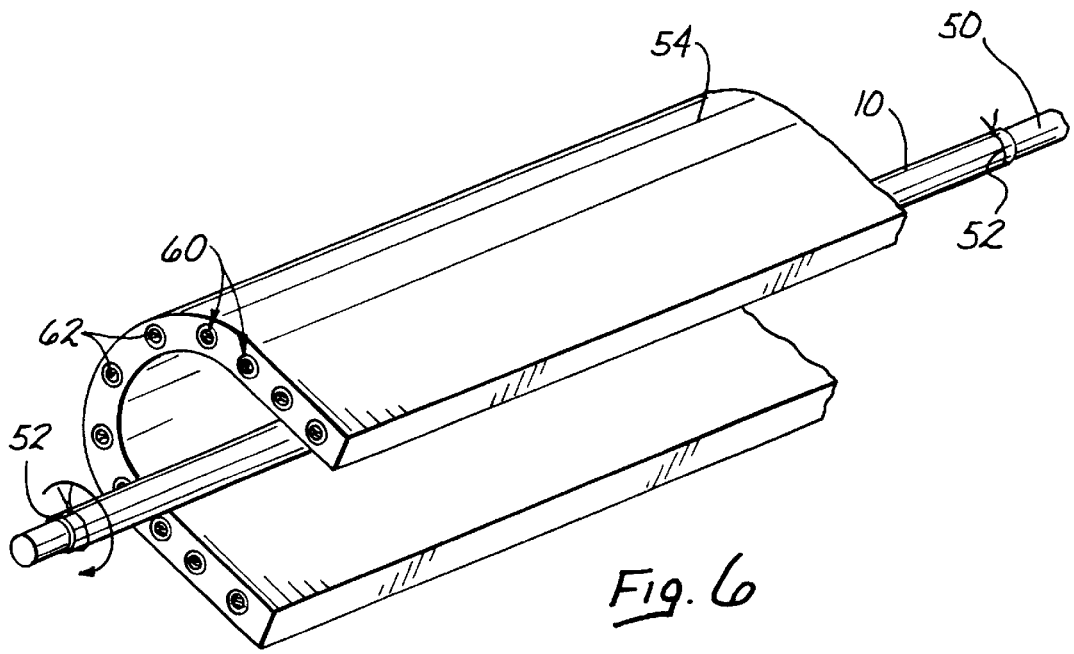
FIG. 6 is a perspective view of an alternative heating apparatus which is useable in the manufacture of the integrally stented PTFE grafts of the present invention.

Another alternative apparatus which may be utilized for the heating step shown schematically in FIG. 4f, is the U-shaped aluminum block heater shown in FIG. 6. This aluminum block heater is formed of a solid aluminum plate or block 54 formed into a generally U-shaped configuration, and having a plurality of bore holes 60 formed longitudinally therein and extending at least part way therethrough. Elongate, cylindrical, electric heaters 62, such as those commercially available from the Watlow Electric Company, 12001 Lackland Road, St. Louis, Mo. 63146, are inserted into the bore holes 60, and such heaters 62 are heated to a temperature which will cause the inner surface of the U-shaped aluminum heater block 54 to be maintained at approximately 300° C. or greater. It will be appreciated that other types of heating apparatus, such as electrical strip heaters mounted on the outer surface of the U-shaped block 54, may be useable as an alternative to the bore holes 60 and cylindrical heaters 62 described herein.

After the U-shaped block 54 has been heated to the desired temperature, the mandrel 50, having the graft 10 and ligatures 52 disposed thereon, is inserted into the U-shaped inner region of the block 54, and is rotated, therein so as to accomplish the desired heat fusing of the tubular base graft 12, outer tape layer 16 and PTFE coating 20 of the stent 14.

In many applications, it will be desirable to post-flex and re-expand the stented graft 10 to ensure that the stented graft 10 is capable of undergoing full radial compression and full radial expansion, over it's complete range of intended diameters.

To accomplish this post-flexing and re-expansion of the stented graft 10, the stented graft 10 is removed from the mandrel 50 and is held in a heated environment, such as in the inner space of the U-shaped heater device shown in FIG. 6. Thereafter, the opposite ends of the stent 14 are pulled longitudinally away from each other to thereby radially contract the stented graft 10 to it's minimal radially compressed diameter $D_1$. Thereafter, the stented graft 10 is allowed to self-expand. If this self-expansion of the stented graft 10 does not result in return of the stented graft 10 to its fully radially expanded diameter $D_2$, the stented graft 10 may then be re-advanced onto the mandrel 50 to thereby force the stented graft 10 to reassume it's full radially expanded configuration of diameter $D_2$.

Thereafter, when the graft is again removed from the mandrel 50, the stented graft 10 will be rendered capable of being radially compressed to it's fully compressed diameter $D_1$, and subsequently self-expanded to it's full radially expanded diameter $D_2$.

F. Assembly and Construction of Internally Stented PTFE Tube Graft

In a first alternative embodiment of the invention, the inner base graft 12 may be eliminated or excluded, thereby providing a modified version of the stented graft 10 comprising only the stent 14 and outer tubular layer 16.

In this first alternative embodiment, the above-described manufacturing method is performed as described without the tubular base graft 12, thereby forming a modified version of the stented graft 10 wherein the outer tubular layer 16 of PTFE is fused only to the stent 14.

In embodiments wherein the stent 14 is coated with a polymer coating such as PTFE, the presence of such coating on the stent 14 will provide lubricity and biocompatability, which may render such internally stented graft suitable for use in applications wherein the exposed stent 14 will come in direct contact with biological fluid or blood flowing through the graft, thereby avoiding the need for use of the internal base graft 12.

Thus, this first alternative embodiment of the present invention includes all possible embodiments wherein only the outer tubular layer 16 is utilized in conjunction with the stent 14, to provide an internally stented graft 10 which is devoid of any internal tubular base graft 12.

G. Assembly and Construction of Externally Stented PTFE Tube Graft

In a second alternative embodiment of the invention, the outer tubular layer 16 may be excluded or eliminated, thereby providing an externally stented PTFE tube graft which comprises only the stent 14 and the inner-base tube 12.

In this second alternative embodiment, the above-described manufacturing method is performed as described without the outer tubular layer 16. This results in the formation of a modified version of the stented graft 10, comprising only the inner base graft 12 and the stent 14.

In embodiments wherein the stent 14 is coated with a polymer coating, such as PTFE, the presence of such coating on the stent 14 will provide for enhanced biocompatability, which may render such externally stented graft suitable for implantation in blood vessels or other tubular anatomical passageways wherein the exposed exterior of the coated stent 14 comes in direct contact with vascular tissue or other tissue of the body, thereby avoiding the need for use of the outer tubular layer 16.

Thus, this second alternative embodiment of the present invention includes all possible embodiments wherein only the inner base graft 12, is utilized in conjunction with the stent 14, to provide an externally stented graft 10 which is devoid of any outer tubular layer 16.

It will be appreciated that the invention has been described hereabove with reference to certain presently preferred embodiments of the invention. Various additions, deletions, alterations and modifications may be made to the above-described embodiments without departing from the intended spirit and scope of the invention. Accordingly, it is intended that all such reasonable additions, deletions, modifications and alterations to the above described embodiments be included within the scope of the following claims.

What is claimed is:

1. A method for manufacturing an integrally stented, tubular, PTFE graft that is alternately deployable in a radially compact configuration having a first diameter and a radially expanded configuration having a second diameter, said method comprising the steps of:
   a) extruding a PTFE paste to form a tubular PTFE extrudate;
   b) longitudinally expanding the tubular PTFE extrudate to form a tubular base graft;
   c) positioning the tubular base graft on a generally cylindrical mandrel;
   d) providing a generally cylindrical stent having a longitudinal bore extending therethrough, wherein said stent is alternately radially compressible to a first diameter and radially expandable to a second diameter, said stent having a plurality of lateral openings;
   e) mounting said stent over the tubular base graft positioned upon said mandrel, such that the tubular base graft is coaxially disposed within the longitudinal bore of said stent in abutting contact therewith;
   f) extruding a PTFE paste dispersion as a film, expanding the film, sintering the film between 350° C.–420° C., and forming expanded, sintered PTFE, tape from the film;
   g) wrapping the expanded, sintered PTFE, tape around the exterior of said stent to form an outer tubular layer thereon in abutting contact therewith; and,
   h) at a first predetermined temperature and a first predetermined time, fusing by heating, said base graft, said stent and said outer tubular layer while mounted on and secured to said mandrel, whereby said outer tubular layer and said base graft become attached to one another through said lateral openings thereby forming said stented graft.

2. The method of claim 1 further comprising the additional steps of:
   i) removing the stented, tubular PTFE graft from the mandrel;
   j) radially contracting the stented tubular PTFE graft to its radially compact configuration of said first diameter; and,
   k) subsequently re-expanding the stented tubular PTFE graft to its radially expanded configuration of said second diameter.

3. The method of claim 2 wherein said re-expanding step is carried out by advancing the stented graft in said radially compact configuration onto a mandrel having an outer diameter substantially equal to the inner luminal diameter of the stented graft in said radially expanded configuration.

4. The method of claim 1 wherein said stent is provided with a plastic coating that will adhere to PTFE when heated, and wherein fusing by heating step further comprises causing said outer tubular layer and the tubular base graft to become adherent to said plastic coating.

5. The method of claim 4 wherein said plastic coating on said stent is a PTF coating.

6. The method of claim 5 wherein said PTFE coating is formed on said stent by the steps of:
   immersing the stent in an aqueous PTFE dispersion;
   removing the stent from the aqueous PTFE dispersion; and,
   drying the aqueous PTFE dispersion which remains on the stent to form said PTFE coating thereon.

7. The method of claim 1 wherein said wrapping step further comprises helically wrapping PTFE tape in overlapping fashion around the exterior of said stent.

8. The method of claim 7 wherein said PTFE tape has a width of ½ inch, and wherein said tape is helically wrapped such that 6–8 revolutions of tape are applied per longitudinal inch of the stented graft.

9. The method of claim 7 wherein said helical wrapping of said tape is performed twice first in one direction and then in the opposite direction.

10. The method of claim 7 wherein said helical wrapping of said tape results in the formation of a tubular outer layer which comprises eight layers of said tape.

11. The method of claim 7 wherein said helical wrapping of said tape is initially performed in a first direction, and subsequently performed in a second direction, opposite said first direction.

12. The method of claim 1 further comprising the step of:
   depositing polymer particles between said tubular base graft and said outer tubular layer to facilitate attachment of said tubular base graft to said outer tubular layer and to said stent.

13. The method of claim 12 wherein said polymer particles are PTFE.

14. The method of claim 12 wherein said depositing of said polymer particles is carried out by depositing an aqueous polymer suspension between said tubular base graft and said outer tubular layer.

15. The method of claim 12 wherein said polymer particles are deposited by rolling the mandrel having said tubular base graft and said stent disposed thereon in powdered polymer resin to accomplish deposition of said polymer particles on the stent and the outer surface of the tubular base graft.

16. The method of claim 15 wherein said powdered polymer resin is PTFE.

17. The method of claim 1 further comprising the step of:
affixing the ends of the tubular outer layer, and tubular base graft to the mandrel to prevent longitudinal shortening during the step of fusing by heating.

18. A method of manufacturing an externally stented, tubular, PTFE graft which is alternately deployable in a radially compact configuration having a first diameter and a radially expanded configuration having a second diameter, said method comprising the steps of:
a) extruding a PTFE paste to form a tubular PTFE extrudate;
b) longitudinally expanding the tubular PTFE extrudate to form a tubular base graft;
c) completely sintering the tubular base graft;
d) positioning the expanded, completely sintered tubular base graft on a generally cylindrical mandrel;
e) providing a generally cylindrical stent which is alternately radially compressible to a first diameter and radially expandable to a second diameter, said stent having a plurality of lateral openings therein;
f) positioning the generally cylindrical stent over the tubular base graft, upon the mandrel, such that the tubular base graft is coaxially disposed within the stent, and is in abutting contact therewith; and
g) heating the mandrel-borne base graft and stent to cause the tubular base graft to become affixed to the stent, thereby forming an externally stented, tubular PTFE graft.

19. The method of claim 18 further comprising the additional steps of:
h) removing the externally stented, tubular PTFE graft from the mandrel;
i) causing the internally stented tubular PTFE graft to be reduced to its radially compact configuration of said first diameter; and,
j) subsequently fully re-expanding the stented tubular PTFE graft to said radially expanded configuration of said second diameter.

20. The method of claim 19 wherein the step of fully re-expanding is carried out by advancing the externally stented PTFE tube graft onto a mandrel which has an outer diameter of the externally stented PTFE tube graft in its radially expanded configuration of said second diameter.

21. The method of claim 18 wherein the step of providing a generally cylindrical stent further comprises coating the stent with a polymer coating which will adhere to PTFE when heated, and wherein the step of heating causes the tubular base graft to become adherent to the polymer coating formed on the stent.

22. The method of claim 21 wherein said polymer coating on said stent is a PTFE coating.

23. The method of claim 21 wherein said polymer coating is formed on said stent by the steps of:
immersing the stent in an aqueous particle dispersion;
removing the stent from the aqueous particle dispersion; and,
drying the aqueous polymer dispersion which remains on the stent to form said polymer coating thereon.

24. The method of claim 23 wherein said aqueous polymer particle dispersion is an aqueous dispersion of PTFE particles.

25. The method of claim 21 wherein said polymer coating is formed on the stent by electron beam deposition.

26. The method of claim 18 further comprising the step of:
affixing the ends of said base graft and said stent to said mandrel to prevent longitudinal shortening during the step of heating.

27. The method of claim 1 wherein said stent is a self-expanding stent.

28. The method of claim 27, wherein said self-expanding stent comprises a shape memory alloy that can alternately exist in a first and a second crystalline state, wherein said stent assumes a radially expanded configuration when said shape memory alloy is in said first crystalline state, and a radially compact configuration when said shape memory alloy is in said second crystalline state.

29. The method of claim 1 wherein said stent is a pressure-expandable stent.

30. The method of claim 1, wherein said first predetermined temperature is about 350°–370° C. and said first predetermined time is up to about 30 minutes.

31. The method of claim 30, wherein said first predetermined temperature is about 363° C.

32. The method of claim 2, wherein said re-expanding step comprises self-expansion.

33. The method of claim 6, further comprising heating said stent with said dried PTFE coating thereon at about 350°–370° C. for up to about 10 minutes.

34. The method of claim 1, wherein the step of sintering the extruded PTFE paste dispersion film is done at a temperature of about 370° C.

35. The method of claim 1, wherein the step of sintering the extruded PTFE paste dispersion film is done at a temperature of about 390° C.

36. The method of claim 1, wherein the step of sintering the extruded PTFE paste dispersion film is done at a temperature of about 410° C.

37. The method of claim 1, further comprising the step of:
depositing polymer particles between the tubular base graft and the outer tubular layer which are subsequently melted during the step of fusing by heating to promote attachment of the tubular base graft to the outer tubular layer.

38. The method of claim 37 wherein said polymer particles are PTFE.

39. The method of claim 37 wherein the step of depositing comprises applying a liquid polymer particle dispersion to one of said base graft and said outer tubular layer, prior to assembly thereof.

40. The method of claim 37 wherein the step of depositing comprises depositing polymer particles between said tubular base graft and said outer tubular layer by applying a liquid dispersion of polymer particles to the exterior of said outer tubular layer, such that the polymer particles contained within the dispersion will migrate inwardly through the outer tubular layer.

41. A method for manufacturing an integrally stented, tubular, PTFE graft that is alternately deployable in a radially compact configuration having a first diameter and a radially expanded configuration having a second diameter, said method comprising the steps of:
   a) extruding a PTFE paste to form a tubular PTFE extrudate;
   b) longitudinally expanding the tubular PTFE extrudate to form a tubular base graft;
   c) positioning the tubular base graft on a generally cylindrical mandrel;
   d) providing a generally cylindrical stent having a longitudinal bore extending therethrough, wherein said stent is alternately radially compressible to a first diameter and radially expandable to a second diameter, said stent having a plurality of lateral openings;
   e) mounting said stent over the tubular base graft positioned upon said mandrel, such that the tubular base graft is coaxially disposed within the longitudinal bore of said stent in abutting contact therewith;
   f) helically wrapping the expanded, sintered PTFE, tape around the exterior of said stent, in a first direction and then in a second opposite direction, to form an outer tubular layer thereon in abutting contact therewith; and,
   g) at a first predetermined temperature and a first predetermined time, fusing, said base graft, said stent and said outer tubular layer while mounted on and secured to said mandrel, whereby said outer tubular layer and said base graft become attached to one another through said lateral openings thereby forming said stented graft.

42. The method of claim 41 wherein said helical wrapping of said tape is performed twice in the first direction and then once in the second direction.

43. The method of claim 41 wherein said PTFE tape has a width of ½ inch, and wherein said tape is helically wrapped such that 6–8 revolutions of tape are applied per longitudinal inch of the stented graft.

44. The method of claim 41 wherein said helical wrapping of said tape results in the formation of an outer tubular layer which comprises eight layers of said tape.

* * * * *